United States Patent
Viöl

(10) Patent No.: US 8,103,340 B2
(45) Date of Patent: Jan. 24, 2012

(54) TREATMENT OF BIOLOGICAL MATERIAL CONTAINING LIVING CELLS USING A PLASMA GENERATED BY A GAS DISCHARGE

(75) Inventor: Wolfgang Viöl, Adelebsen (DE)

(73) Assignee: HAWK Hochschule fur angewandte Wissenschaft und Kunst, Hildesheim (DE)

( * ) Notice: Subject to any disclaimer, the term of this patent is extended or adjusted under 35 U.S.C. 154(b) by 1105 days.

(21) Appl. No.: 11/291,354

(22) Filed: Dec. 1, 2005

(65) Prior Publication Data

US 2006/0084158 A1 Apr. 20, 2006

Related U.S. Application Data

(63) Continuation-in-part of application No. PCT/EP2004/005988, filed on Jun. 3, 2004.

(30) Foreign Application Priority Data

Jun. 3, 2003 (DE) .................................. 103 24 926

(51) Int. Cl.
*A61L 2/14* (2006.01)
*A61N 1/00* (2006.01)

(52) U.S. Cl. ........................... 607/2; 604/25; 435/173.1
(58) Field of Classification Search .................. None
See application file for complete search history.

(56) References Cited

U.S. PATENT DOCUMENTS

| | | | | |
|---|---|---|---|---|
| 5,843,079 A | * | 12/1998 | Suslov | 606/43 |
| 5,866,082 A | | 2/1999 | Hatton et al. | 422/186.07 |
| 6,197,026 B1 | | 3/2001 | Farin et al. | 606/49 |
| 6,213,999 B1 | * | 4/2001 | Platt et al. | 606/27 |
| 6,543,460 B1 | * | 4/2003 | Denes et al. | 134/1.1 |
| 6,780,178 B2 | * | 8/2004 | Palanker et al. | 606/34 |
| 6,818,102 B1 | | 11/2004 | Viol | 204/164 |
| 2005/0143775 A1 | | 6/2005 | Viol et al. | 607/2 |

FOREIGN PATENT DOCUMENTS

| | | | |
|---|---|---|---|
| GB | 2 378 387 A | | 2/2003 |
| JP | 199947240 | | 2/1999 |
| RU | 2138213 | * | 9/1999 |
| WO | WO 87/07248 | | 12/1987 |
| WO | WO 01/39944 | * | 6/2001 |

OTHER PUBLICATIONS

Stoffels et al., http:// web.archive.org/ web/ 20040330151154/ http:// www .phys.tue.nl/EPG/epghome/projects/bmtweb.htm , pp. 1-11.*
Abramov et al., "Device for Coagulation and Stimulation of Healing of Wound Defects of Biological Tissues", RU 199990927 C1 2138213, English translation, pp. 1-7.*
Abramov et al., "Device for Coagulation and Stimulation of Healing Wound Defects of Biological Tissues", RU 19990927 C1 2138213, English Translation, pp. 1-7. 1999.*
Stoffels et al., http:// web.archive.org/ web/ 20040330151154/ http:// www .phys.tue.nl/EPG/epghome/projects/bmtweb.htm , pp. 1-11. 2004.*

* cited by examiner

*Primary Examiner* — Laura Schuberg
(74) *Attorney, Agent, or Firm* — Thomas, Kayden, Horstemeyer & Risley, LLP

(57) ABSTRACT

In order to treat a biological material (1) containing living cells with a plasma (4) generated by a gas discharge at atmospheric pressure (9) an electrode (3) is arranged at a distance to the biological material (1). Further, a solid body dielectric (2) is arranged between the electrode (3) and the biological material (1), directly in front of the electrode (3) and at a distance to the biological material (1). Then a high alternating voltage consisting of separated high voltage pulses of alternating polarity is applied to the electrode (3) for igniting and maintaining a dielectric barrier gas discharge within a region between the dielectric (2) and the biological material (1).

24 Claims, 2 Drawing Sheets

US 8,103,340 B2

TREATMENT OF BIOLOGICAL MATERIAL CONTAINING LIVING CELLS USING A PLASMA GENERATED BY A GAS DISCHARGE

CROSS REFERENCE TO RELATED APPLICATIONS

This application is a continuation in part of International Patent Application PCT/EP 2004/005988 filed Jun. 3, 2004, entitled "Behandlung von lebende Zellen enthaltenden biologischen Materialien mit einem durch eine Gasentladung erzeugten Plasma" and claiming priority to German Patent Application No. DE 103 24 926.5, now German Patent No. DE 103 24 926, filed Jun. 03, 2003 and having the same title as the international patent application.

FIELD OF THE INVENTION

The present invention generally relates to a method of and an apparatus for treating biological material containing living cells using a plasma generated by a gas discharge.

Here and in this whole description of the present invention, the term "plasma" does not refer to a blood plasma, but to a physical plasma, i.e. a particular electrically conductive state of a gas or a gas mixture, like it is generated by a so-called gas discharge.

BACKGROUND OF THE INVENTION

Treating organic materials using a plasma which is generated by a gas discharge at atmospheric pressure is for example known from U.S. Pat. No. 6,818,102. Here, wooden surfaces are modified by a dielectric barrier discharge. However, no indications of treating biological material containing living cells are given here.

A method of and a device for treating biological material containing living cells using a plasma generated by a gas discharge are known from U.S. Pat. No. 5,866,082 A. Here, a glass bulb filed with neon gas forms a dielectricum. An electrode is arranged on the back of the glass bulb, to which a high alternating voltage generator applies an high alternating voltage to create a gas discharge both in the neon gas within the glass bulb and between the glass bulb and a skin surface. The known method and the known apparatus serve for treating the skin, above which the gas discharge is ignited, with ozone which is formed by a gas discharge in oxygen containing air. The electric power which is supplied by the high alternating voltage generator to the electrode is in the range of several 10 Watt. Thus, it is important, to avoid a direct contact of the skin with the electrode, even if the intermediate glass bulb is destroyed. To this end, a shielding of electrically isolating material protrudes beyond the electrode, which shielding laterally surrounds the glass bulb. Electric energy is supplied to the known apparatus via the usual power network. The known apparatus and the known method are intended for a large area treatment of the skin. The dimensions of the electrode and the glass bulb does not allow for local treatments. Ozone treatment of human skin serves for cosmetic ends in that bacteria at the skin surface are eliminated.

An improvement of the apparatus known from U.S. Pat. No. 5,866,082 A is described in GB 2,378,387 A. This improvement shall solve the problem which is connected with a possible break of the glass bulb. To this end, a protection coating is provided to the glass bulb, which protection coating comprises openings to enable the gas discharge between the glass bulb and the skin surface. It can be taken from GB 2,378,287 A that the glass bulb is no longer able to conduct electrical energy for the gas discharge as soon as it breaks and the neon gas disappears.

An electro surgical instrument is known from DE 198 20 240 A1, which instrument forms a plasma by means of a barrier free gas discharge within an inert gas or gas mixture comprising no oxygen. The main effect of the plasma on the tissue treated with this instrument is thermal; i.e. a thermal coagulation takes place. A barrier-free electric discharge can only be realized within a very high frequency range and with comparatively high electric power.

In the field of deontology the treatment of dental caries with ozone is known. To this end, a limited area above that site of a dent which has caries is purged with ozone. The ozone is generated in a stationary apparatus and supplied via a tube to a small treating dome arranged at an oral probe. The ozone is sucked off from the treating dome again, and unused ozone is neutralized in a filter. Overall, the known apparatus for caries treatment is quite complicated.

Thus, there is a need for a method of and an apparatus for treating biological material containing living cells using a plasma generated by a gas discharge with little energy consumption, with little danger of accident and also in small spatially limited areas.

SUMMARY OF THE INVENTION

In one aspect the present invention relates to a method of treating a biological material containing living cells with a plasma generated by a gas discharge at atmospheric pressure, the method comprising the steps of arranging an electrode at a distance to the biological material; of arranging a solid body dielectric between the electrode and the biological material, directly in front of the electrode and at a distance to the biological material; and of applying a high alternating voltage consisting of separated high voltage pulses of alternating polarity to the electrode for igniting and maintaining a dielectric barrier gas discharge within a region between the dielectric and the biological material, an electric power of the gas discharge being smaller than 10 W.

In another aspect the present invention relates to an apparatus for treating a biological material containing living cells with a plasma generated by a gas discharge at atmospheric pressure, the apparatus comprising an electrode; a solid body dielectric arranged between the electrode and the biological material, directly in front of the electrode and at a distance to the biological material; and a high alternating voltage generator connected to the electrode for generating a high alternating voltage consisting of separated high voltage pulses of alternating polarity, which high alternating voltage ignites and maintains a dielectric barrier gas discharge between an active surface of the dielectric and the biological material, an electric output power of the high alternating voltage generator being smaller than 10 W.

In a further aspect the invention relates to an apparatus for treating a biological material containing living cells with a plasma generated by a gas discharge at atmospheric pressure, the apparatus comprising an electrode; a solid body dielectric arranged between the electrode and the biological material, directly in front of the electrode and at a distance to the biological material; and a high alternating voltage generator for generating a high alternating voltage applied to the electrode, which high alternating voltage ignites and maintains a dielectric barrier gas discharge between an active surface of the dielectric and the biological material, the high alternating voltage generator generating pulse packets of short time high voltage pulses of alternating polarity at a voltage in the range of 5 to 15 kV, at a pulse energy of less than 1 mJ per pulse, at an interval of time between two successive pulses within each pulse packet of 100 to 10,000 ns, at a pulse packet repetition frequency of less than about 10,000 Hz, and at an electric output power of 0.05 to 2.0 W per $cm^2$ of the active surface of the dielectric.

In the method and the apparatus according to the invention the dielectric material is a solid state dielectric material which is arranged directly, i.e. without gap or a clearance existing between them, in front of the electrode to which the high alternating voltage is applied for igniting and maintaining the gas discharge over the biological material to be treated. Thus, there is no complicated gas filed glass bulb. Instead, the dielectric is a simple solid body. The dielectric may even bee glass, but it is solid glass then. The dielectric may also be made of ceramics or of such plastics which are sufficiently inert with regard to the effects of the gas discharge. As compared to a gas filed glass bulb, the dielectric in the new method and in the new apparatuses may be very thin. Its typical thickness is a few millimeters, i.e. about 5 mm at maximum. Preferably, the maximum thickness of the electric is about 3 mm. Depending on the material of the dielectric, a thickness of the dielectric of, for example, 0.5 mm or less may be sufficient. The little thickness of the dielectric makes it easier to ignite and maintain the gas discharge over a small defined area of the biological material to be treated. Avoiding an additional gas room between the dielectric and the electrode or within the dielectric reduces the electric energy required for the gas discharge. In the invention, the dielectric barrier discharge creates a plasma which is essentially cold, a typical temperature in the region of the gas discharge being about 40° C. Thus, the thermal effects of the gas discharge are limited. The chemical and microphysical effects caused by the plasma are more important. When the gas discharge takes place in the presence of oxygen, an essential effect of the gas discharge is based on the production of free oxygen, i.e. atomic or excited oxygen, which is highly oxidative, so that, for example, microorganisms at the surface of the biological material to be treated may be purposefully eliminated. The microorganisms to be eliminated may for example consist of caries attacking a dent. In this regard, free oxygen is even more effective than ozone. Based on the reactivity of the oxygen, surface layers of tissues which may be degenerated tissues, may be extinct. Despite the essentially non-thermal effect of the plasma of the invention, even an oxidative coagulation may be effected to stop bleeding, for example.

Particularly, the gas discharge of the invention may be maintained over a surface of the biological material, which is smaller than 100 $mm^2$, preferably smaller than 50 $mm^2$; more generally, the surface area of the biological material which is treated at the same point in time is between 0.005 and 10 $cm^2$. The surface area covered by the gas discharge, which is the total cross sectional area of the region within which the gas discharge takes place, and not only the cross sectional area of single discharge filaments, may also be only a few $mm^2$ in size, so that a targeted local treatment of the biological material is possible.

To avoid any thermal influence of the plasma onto the biological material to be treated, a gas flow can be directed over the biological material in the area of the gas discharge, which cools the biological material. The gas flow can also be used to remove reaction products out of the region of the plasma, or to purposefully introduce chemical reagents into the region of the plasma.

To avoid that free oxygen gets into the surroundings of the gas discharge without control, it is preferred, to suck of gas out of the area of the gas discharge. Sucking off the gas may be done in a coaxial arrangement with regard to the electrode, for example, through a ring shaped volume around the electrode or through a tube formed by the electrode so that the apparatus is very slim at its active tip.

The gas flow may also be used to ignite the gas discharge within a gas or a gas mixture, the composition of which differs from ambient air, to purposefully initiate certain reactions of the biological material to be treated with certain substances contained in the gas or gas mixture.

The electric power of the gas discharge of the invention is typically much smaller than 10 W. Mostly, it is smaller than 5 W, and, preferably, it is about 1 Watt or even smaller.

It is particularly preferred, if the alternating high voltage is generated as pulse packets each consisting of at least one bipolar voltage pulse, i.e. of two successive short time pulses of opposite polarity. Each pulse packets may comprise more than one bipolar pulse. One bipolar pulse per pulse packet, however, is preferred. The pulse packets may be separated from each other by a much longer interval of time than the successive short time pulses of opposite polarity or the bipolar pulses within each pulse packet. The pulse duration of each single pulse can be between 100 and 500 ns; preferably, it is between 200 and 400 ns. The intervals in time between these single pulses within each pulse packet can be from 100 to 10,000 ns; preferably, they are about 1000 ns. The consecution of the single pulses within each pulse packet corresponds to a pulse repetition frequency of up to 3,000 kHz. Preferably, however, the repetition frequency of the pulse packets, and thus the number of actual pulses per time unit is much lower. Typically, a pulse packet repetition frequency is less than about 10,000 Hz; preferably, it is less than about 1000 Hz, and for example it is in a range from 200 to 300 Hz. For special applications, very short single high voltage pulses may also be applied to the electrode at even longer intervals in time. These pulses may have a duration of about 10 ns. The maximum voltage of each single pulse is typically in a range of about 5 to about 15 kV. This voltage is applied with alternating polarity; i.e. the voltage difference from pulse to pulse of different polarities is 10 to about 30 kV. The electric energy per pulse is generally less than 1 mJ; particularly, it can be about 0.3 mJ per bipolar pulse. The power density of the gas discharge may be in the range of 0.1 to 1.0 Watt per $cm^2$ cross sectional area of the gas discharge. These data ensure that no unwanted damages or severe irritations occur, when the gas discharge is applied to treat the skin of a human patient, for example. As viewed in total, the bipolar pulses cause no electric charging or current which is recognized by a human patient, as they consist of two pulses of opposite polarity which follow each other much too fast for being noticed separately. Further, the above data may be easily realized using commercially available electronic semiconductor units. Thus, a high alternating voltage generator of the new apparatus can be manufactured at comparatively low cost. Because of the bipolarity of the pulses it is absolutely not required to connect any of the biological material and the high alternating voltage generator to earth, or to provide a return circuit between the biological material and the high alternating voltage generator.

To avoid an unwanted contact of the biological material with the active surface of the dielectric, the area of the gas discharge can laterally be shielded by electrically isolating material which is not subject to electrostatic charging. This is, for example, useful, if the gas discharge is ignited within an oral cavity for treating a dent attacked by caries, where the danger exists that the tongue of the patient gets into contact with the dielectric. Also a direct contact of the dent to be treated with the dielectricum is not desired.

It is a particular advantage of the present invention, that it can be realized as a battery-powered unit. I.e. the alternating voltage for igniting and maintaining the gas discharge can be generated using electric energy out of a commercially available accumulator. Thus, the new apparatus for carrying out the new method can by designed as a compact hand-held unit.

So far as an active surface of the dielectric is indicated in the definition of the new invention in the appended claims, this active surface of the dielectricum is the surface of the dielectricum facing the biological material in using the apparatus, over which an electric field strength is generated upon applying the high alternating voltage to the electrode, which is sufficient for igniting and maintaining the gas discharge. What parts of the surface of the dielectricum may be regarded as the active surface of the dielectricum in a particular case will depend on the geometry of the electrode and of the dielectric, and will naturally also be influenced by the high alternating voltage applied to the electrode. In practice, however, the extend of the active surface of the dielectric can easily be determined in that it is looked for where the gas discharge takes place in front of the surface of the dielectric.

Particular applications of the new method and the new device include the treatment of pruritus like for example associated with neurodermatitis and mosquito bites. After the plasma treatment such a pruritus is essentially reduced. Eliminating viruses by the skin treatment may for example be used to treat verrucae, zoster, or herpes. By dental treatment according to the new method and with the new apparatus a dent can also be prepared for caries prophylaxis in that it is cleaned from saliva remainders, in that bacteria and viruses are eliminated, and in that its dental surface is activated or in that the surface energy of the dent is enhanced. This pre-treatment has the effect that a successive coating of the dent with a fluor protector which seals fissures or the like is more effective and longer lasting. The coating of the dent may also be prepared directly using the plasma in that, for example, methane or silanes are added to the gas of which the plasma is generated. Fluorinated gases like tetrafluoromethane may also be added.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
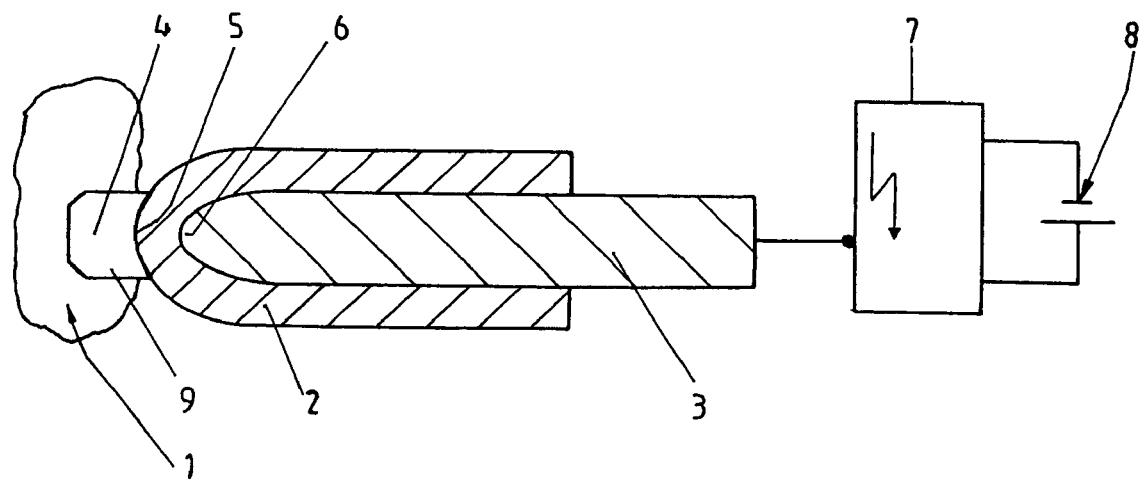
FIG. 1 schematically shows the construction of a first embodiment of the new apparatus during execution of the new method.

Referring now in greater detail to the drawings, FIG. 1 illustrates an apparatus according to the invention which comprises, as its main components, a pin-like electrode 3, a dielectric 2 covering the rounded tip 6 of the electrode 3 and a high alternating voltage generator 7 generating an alternating high voltage which is applied to the electrode 3 during operation of the apparatus. These components of the apparatus may be parts of a hand-held unit including one or a plurality of accumulators 8 for supplying electrical energy to the high alternating voltage generator 7. The high alternating voltage generator 7, however, can also be supplied with electric energy by a mains supply circuit. This mains supply circuit or a unit consisting of the mains supply circuit and the high alternating voltage generator may be designed as a stationary unit. On the one hand, the dielectric 2 serves for isolating the electrode 3. On the other hand it serves at a dielectric barrier for a gas discharge 9 which is ignited between the dielectric 2 and the surface of a biological material 1 upon applying the high alternating voltage to the electrode 3, and which creates a physical plasma 4 above the surface of the biological material 1. If the gas discharge takes place in the presence of oxygen, like for example ambient air oxygen, the plasma includes free oxygen, i.e. high reactive free oxygen atoms, which chemically influence the biological material 1 at its surface. The dielectric barrier for the gas discharge 9 formed by the dielectric 2 results into a cold plasma 4. I.e. the thermal effects of the plasma 4 may by neglected at least over shorter intervals of time within which the plasma acts upon the biological material 1 of some few seconds up to several seconds. The cross sectional area of the gas discharge 9 is defined by the area within which sufficient electric field strength for maintaining the gas discharge 9 is present between the dielectric 2 and the biological material 1. The corresponding surface of the dielectric 2 is also designated as the active surface of the dielectric 2 here. Outside this active surface the dielectric 2 mainly serves as an isolation of the electrode 3. To this end, the dielectric may also have a purposefully amended composition or a purposefully increased wall thickness outside its active area. Within the active area of the dielectric 2 its wall thickness is typically some few millimeters. The material of the dielectric 2 is preferably ceramic. However, it may also be glass or a plastic which is sufficiently resistant with regard to the plasma 4. The treatment of the biological material 1 by means of the plasma 4 essentially consists of killing cells, for example undesired microorganisms like bacteria or degenerated tissues, at the surface of the biological material 1. This can particularly be done to treat dental caries.

Figure 2:
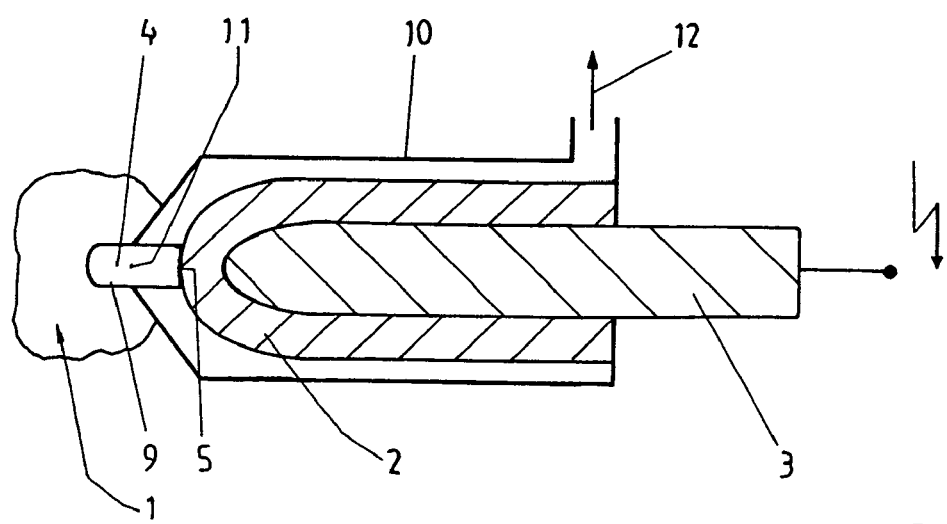
FIG. 2 schematically shows the construction of a second embodiment of the new apparatus during execution of a second embodiment of a new method.

The drawing of the embodiment of the new apparatus shown in FIG. 2 at first differs from that one according to FIG. 1 in that details with regard to the high alternating voltage generator and its supply with electric energy are omitted. The important difference, however, is that a sucking off and isolating housing is arranged around the dielectric 2 but at a distance to the dielectric. The housing has an opening 11 in front of the active area of the dielectric 2, through which gas is sucked off the region of the gas discharge 9. By means of sucking off gas, uncontrolled setting free of free oxygen out of the plasma 4 into the surroundings of the gas discharge 9 is avoided. Instead, such oxygen can be neutralized in suitable filters after being sucked off. The material of the isolating and sucking off housing 10 is electrically isolating and not subject to electrostatic charging in such a way that it is ensured that neither a gas discharge is ignited within the clearance between the dielectric 2 and the isolating and sucking off housing 10, nor that a direct contact with the isolating and sucking off housing 10 with a conductive object results in the transfer of electric energy. Thus, it is avoided in treating caries within the oral cavity, for example, that the tongue of the patient gets into contact with the dielectric 2 or even with the electrode 3 which would have the result of an unpleasant electric irritation.

Instead of sucking off gas 12 out of the region of the gas discharge 9, a gas can be purposefully supplied into this region, the composition of which deviates from ambient air or which only serves for cooling the surface of the biological material 1. Such a cooling, however, is also achieved by sucking off gas in the apparatus according to FIG. 2. In any case, cooling of the surface of the biological material 1 by means of a gas flow has the result that the effects of the plasma 4 are limited to chemical and microphysical non-thermal effects.

Figure 3:
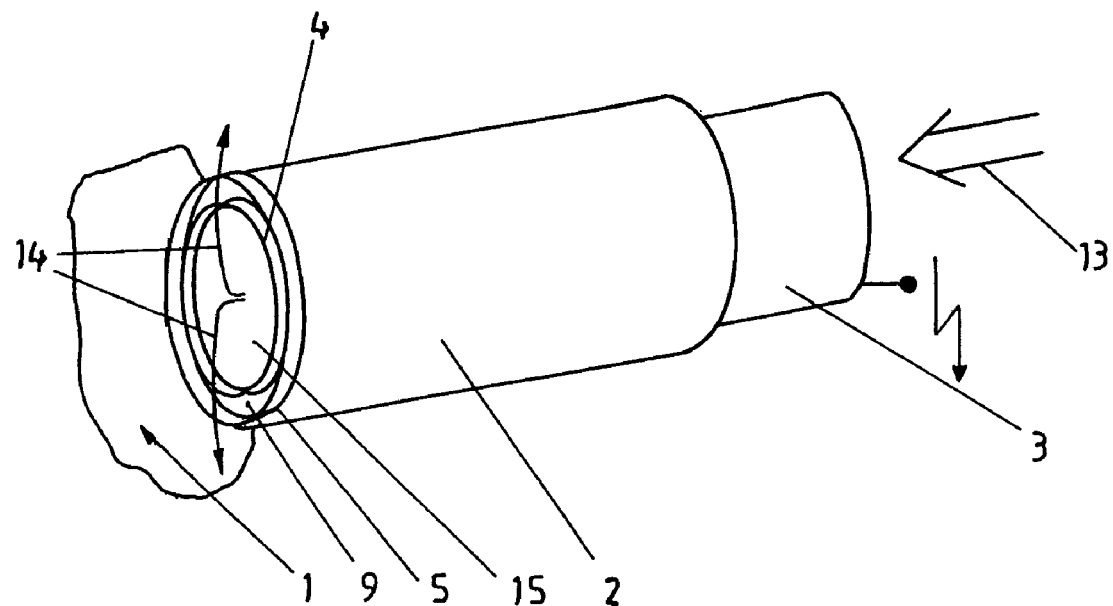
FIG. 3 schematically shows the construction of a further embodiment of the new apparatus during execution of a further embodiment of the new method.

In the embodiment of the apparatus according to FIG. 3, a reaction gas 13 having a special composition deviating from air is blown into the region of the gas discharge 9. Like in FIG. 2, this is carried out in a coaxial arrangement. In FIG. 3, however, the electrode 3 is tube-shaped and both at its interior and its exterior and at its tip 6 covered with the dielectric 2. The resulting active surface area of the dielectric 2 is a ring. I.e. the region of the gas discharge 9 has the shape of a cylinder barrel. In addition to supplying reaction gas 13, gas could also be sucked off the region of the gas discharge 9 in an arrangement according to FIG. 2 to avoid an uncontrolled setting free of, for example, free oxygen into the surroundings of the gas discharge 9 here, too.

Figure 4:
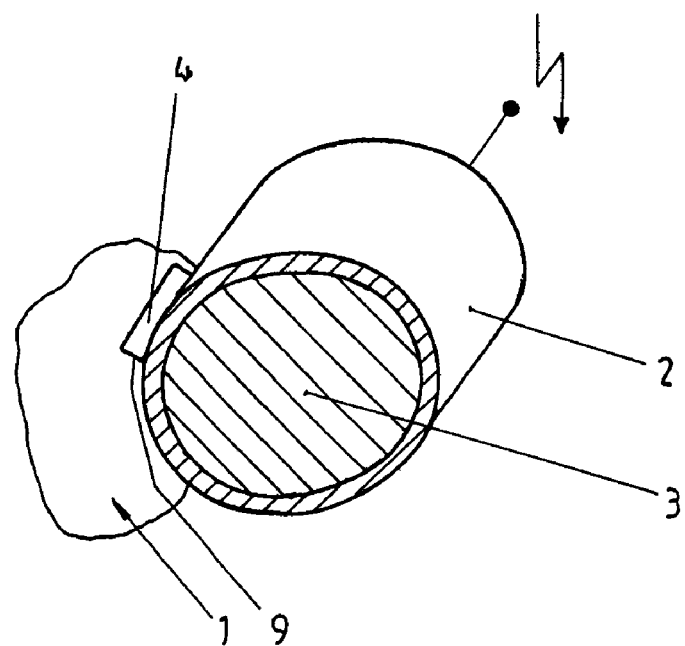
FIG. 4 schematically shows the construction of an even further embodiment of the new apparatus during execution of an even further embodiment of the new method.

FIG. 4 shows an embodiment of the apparatus having a somewhat different geometric arrangement. Here, the rod-shaped electrode 3 is all around covered by the dielectric 2. In a parallel arrangement of the electrode 3 to the surface of the biological material 1, a line-shaped area of the gas discharge 9 is formed, in which the plasma 4 generated. Upon moving the electrode 3 over the surface of the biological material 1, comparatively large areas of the biological material 1 can be treated with the plasma 4, although the surface of the biological material 1 which is treated at one point in time and which corresponds to the active area of the dielectric 2 is always comparatively small. The small size of the region of the gas discharge 9 as well as the dielectric barrier to the gas discharge 9 reduces the energy consumption of the gas discharge 9, which is a precondition for the gas discharge 9 being generated using accumulators, particularly commercially available batteries, as an electric energy supply. At the same time the low electric power of the gas discharge 9 also ensures that the level of any electric irritation which is associated with using the new apparatus, i.e. with the application of the new method even in an extreme case, remains small. This is an important security aspect. A further security aspect is that the dielectric 2 is a solid body dielectric which is located on the electrode 3 without any gap or clearance so that no danger of a direct contact with the electrode 3 is existent, even if the new device is improperly used.

Many variations and modifications may be made to the preferred embodiments of the invention without departing substantially from the spirit and principles of the invention. All such modifications and variations are intended to be included herein within the scope of the present invention, as defined by the following claims.

I claim:

1. A method of treating a biological material containing living cells with a plasma generated by a gas discharge at atmospheric pressure, the method comprising the steps of: arranging an electrode at a distance to the biological material, the biological material residing in a patient, arranging a solid body dielectric between the electrode and the biological material, directly in front of the electrode and at a distance to the biological material of the patient, and applying a high alternating voltage consisting of separated high voltage pulses of alternating polarity to the electrode for igniting and maintaining a dielectric barrier gas discharge within a region between the dielectric and the biological material, an electric power of the gas discharge being smaller than about 10 W, wherein the temperature in the region of the gas discharge is about 40° C. and wherein the plasma eliminates microorganisms on the surface of the biological material.

2. The method of claim 1, wherein the gas discharge is maintained over an area of the biological material which is smaller than about 100 mm$^2$.

3. The method of claim 2, wherein the gas discharge is maintained over an area of the biological material which is smaller than about 50 mm$^2$.

4. The method of claim 1, wherein a gas flow over the biological material is generated in the region of the gas discharge.

5. The method of claim 4, wherein gas is sucked off the region of the gas discharge.

6. The method of claim 5, wherein the gas is sucked off coaxially with regard to the electrode.

7. The method of claim 4, wherein the gas discharge is maintained in a gas, the composition of which deviates from ambient air.

8. The method of claim 7, wherein the gas is selected from pure gases and mixtures thereof.

9. The method of claim 1, wherein the high alternating voltage is applied to the electrode in such a way that the electric power of the gas discharge is smaller than about 5 W.

10. The method of claim 9, wherein the high alternating voltage is generated as separated bipolar high voltage pulses each consisting of two single high voltage pulses of opposite polarity, the pulse repetition frequency of the single high voltage pulses of opposite polarity of each bipolar high voltage pulse being up to about 3,000 kHz.

11. The method of claim 9, wherein the high alternating voltage is generated using electric energy out of an accumulator.

12. The method of claim 1, wherein a voltage of each high voltage pulse is in a range from about 5 to about 15 kV.

13. The method of claim 1, wherein the region of the gas discharge is laterally shielded with a material which is electrically isolating and not subject to electrostatic charging.

14. The method of claim 1, wherein the dielectric barrier gas discharge creates a cold plasma.

15. The method of claim 1, wherein the patient is a human patient.

16. The method of claim 1, wherein the biological material is a tooth.

17. The method of claim 1, wherein the biological material is skin.

18. The method of claim 1, wherein applying the high alternating voltage does not produce an electrically generated biological response in the patient.

19. The method of claim 1, wherein the gas discharge has a power density in the range of 0.1 to 1.0 Watt per cm$^2$.

20. The method of claim 1, wherein the eliminated microorganism is selected from the group consisting of a bacteria and a virus.

21. A method of treating a biological material containing living cells with a plasma generated by a gas discharge at atmospheric pressure, the method comprising the steps of:

arranging an electrode at a distance to the biological material, the biological material residing in a patient, arranging a solid body dielectric between the electrode and the biological material, directly in front of the electrode and at a distance to the biological material of the patient, and applying a high alternating voltage consisting of separated high voltage pulses of alternating polarity to the electrode for igniting and maintaining a dielectric barrier gas discharge within a region between the dielectric and the biological material, an electric power of the gas discharge being smaller than about 10 W, wherein the dielectric barrier discharge creates a cold plasma, wherein the temperature in the region of the gas discharge is about 40° C. and wherein the plasma kills at least one item selected from the group consisting of a bacteria and a virus.

22. The method of claim 21, wherein the patient is a human patient.

23. The method of claim 21, wherein the biological material is a tooth.

24. The method of claim 21, wherein the biological material is skin.

* * * * *